(12) United States Patent
Ruohonen

(10) Patent No.: US 7,720,519 B2
(45) Date of Patent: May 18, 2010

(54) METHOD FOR THREE-DIMENSIONAL MODELING OF THE SKULL AND INTERNAL STRUCTURES THEREOF

(75) Inventor: Jarmo Ruohonen, Helsinki (FI)

(73) Assignee: Elekta Neuromag Oy, Helsinki (FI)

( * ) Notice: Subject to any disclaimer, the term of this patent is extended or adjusted under 35 U.S.C. 154(b) by 471 days.

(21) Appl. No.: 10/529,473

(22) PCT Filed: Oct. 16, 2003

(86) PCT No.: PCT/FI03/00772

§ 371 (c)(1),
(2), (4) Date: Mar. 28, 2005

(87) PCT Pub. No.: WO2004/035135

PCT Pub. Date: Apr. 29, 2004

(65) Prior Publication Data

US 2006/0052687 A1 Mar. 9, 2006

(30) Foreign Application Priority Data

Oct. 17, 2002 (FI) .................................. 20021858

(51) Int. Cl.
*A61B 5/05* (2006.01)

(52) U.S. Cl. ...................... 600/411; 382/128; 600/407; 600/416

(58) Field of Classification Search ................. 600/416, 600/407, 409, 427, 544; 382/128; 345/419; 702/19
See application file for complete search history.

(56) References Cited

U.S. PATENT DOCUMENTS 4,680,856 A 7/1987 Zuccarelli 4,736,751 A * 4/1988 Gevins et al. ............... 600/545

(Continued)

FOREIGN PATENT DOCUMENTS

EP 1 17 6558 A2 1/2002

(Continued)

OTHER PUBLICATIONS

"Model Extraction from Magnetic Resonance Volume Data Using the Deformable Pyramid," Lotjonen et al., *Medical Image Analysis*, vol. 3, No. 4, 1999, pp. 387-406.

(Continued)

*Primary Examiner*—Brian Casler
*Assistant Examiner*—Jonathan G Cwern
(74) *Attorney, Agent, or Firm*—Birch, Stewart, Kolasch & Birch, LLP

(57) ABSTRACT

A method is disclosed in this publication for modeling different internal structures of a head, such as different parts of the brain, the method comprising the step of determining the location of the internal structures, such as the different cerebral parts, of at least one first head in a three-dimensional space by techniques such as magnetic resonance imaging or computer-aided tomography. According to the invention, the external dimensions of at least one second head are determined, and the location data of the internal structures of the first head are scaled in a three-dimensional space to correlate with the external dimensions of the second head, whereby the location data of the internal structures of the second head also become modeled without the need for anatomical images of the second head.

17 Claims, 1 Drawing Sheet

U.S. PATENT DOCUMENTS

Figure 1:
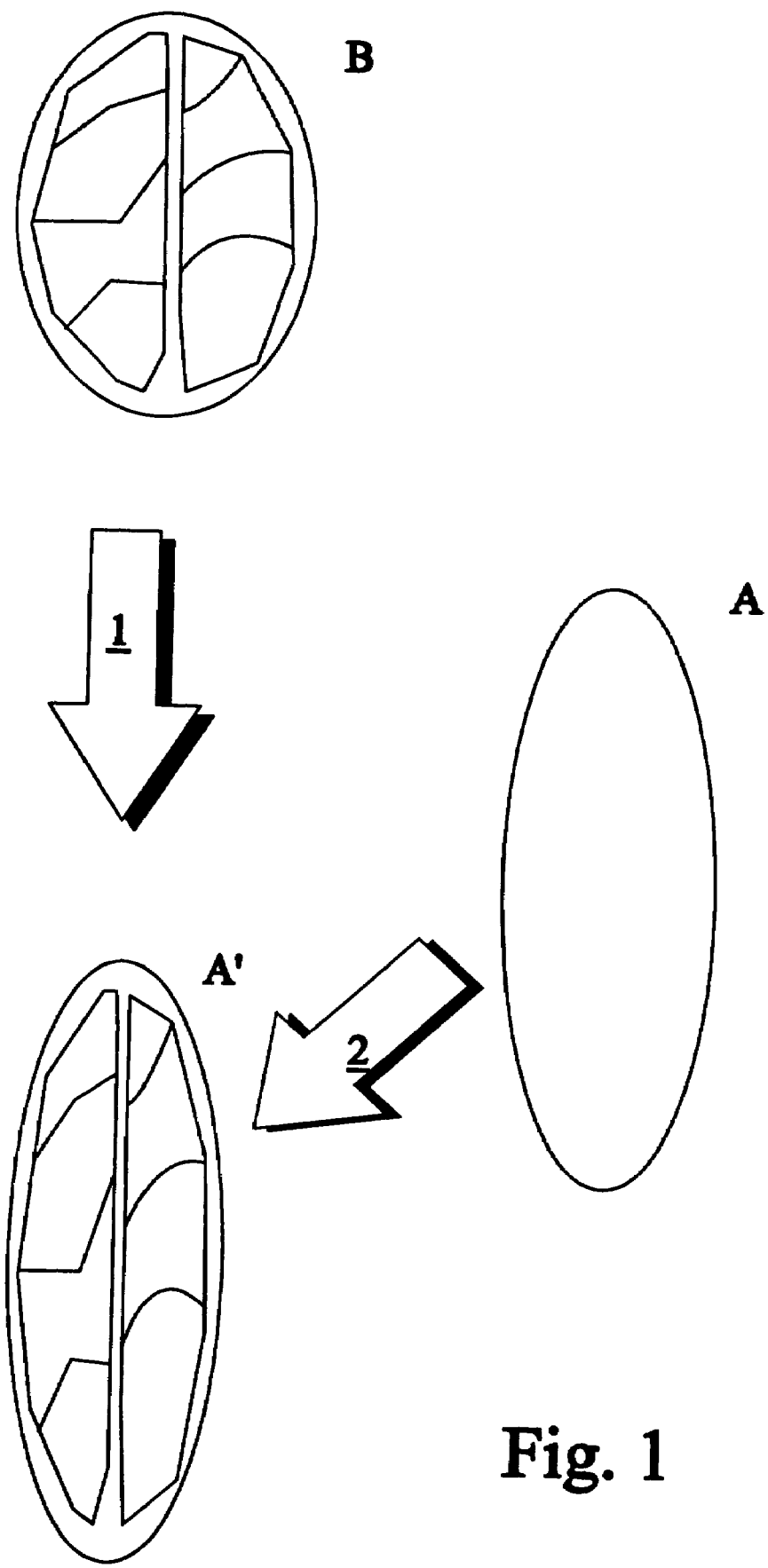

| | | | |
|---|---|---|---|
| 5,119,816 A * | 6/1992 | Gevins | 600/383 |
| 5,291,889 A | 3/1994 | Kenet et al. | |
| 5,331,970 A * | 7/1994 | Gevins et al. | 600/544 |
| 5,871,445 A * | 2/1999 | Bucholz | 600/407 |
| 5,891,034 A * | 4/1999 | Bucholz | 600/426 |
| 6,076,008 A * | 6/2000 | Bucholz | 600/427 |
| 6,226,418 B1 * | 5/2001 | Miller et al. | 382/294 |
| 6,236,875 B1 * | 5/2001 | Bucholz et al. | 600/407 |
| 6,374,135 B1 * | 4/2002 | Bucholz | 600/427 |
| 6,408,107 B1 * | 6/2002 | Miller et al. | 382/294 |
| 6,556,695 B1 * | 4/2003 | Packer et al. | 382/128 |
| 6,633,686 B1 * | 10/2003 | Bakircioglu et al. | 382/294 |
| 6,711,432 B1 * | 3/2004 | Krause et al. | 600/427 |
| 6,856,830 B2 * | 2/2005 | He | 600/513 |
| 7,072,704 B2 * | 7/2006 | Bucholz | 600/407 |
| 7,087,008 B2 * | 8/2006 | Fox et al. | 600/13 |
| 7,191,110 B1 * | 3/2007 | Charbel et al. | 703/11 |
| 7,194,295 B2 * | 3/2007 | Vilsmeier | 600/416 |
| 2002/0087075 A1 * | 7/2002 | Bucholz | 600/429 |
| 2003/0018277 A1 * | 1/2003 | He | 600/544 |
| 2003/0050527 A1 * | 3/2003 | Fox et al. | 600/13 |
| 2003/0073899 A1 | 4/2003 | Ruohonen et al. | |
| 2003/0236487 A1 * | 12/2003 | Knowlton | 604/20 |
| 2004/0125103 A1 * | 7/2004 | Kaufman et al. | 345/419 |
| 2005/0020918 A1 * | 1/2005 | Wilk et al. | 600/439 |
| 2005/0075560 A1 | 4/2005 | Hannula et al. | |
| 2006/0052687 A1 * | 3/2006 | Ruohonen | 600/410 |
| 2007/0038080 A1 * | 2/2007 | Salisbury et al. | 600/427 |

FOREIGN PATENT DOCUMENTS

| | | |
|---|---|---|
| EP | 1176558 A2 | 1/2002 |
| EP | 1 270 043 A1 | 1/2003 |
| WO | WO-93/20749 A1 | 10/1993 |
| WO | WO-99/59106 A1 | 11/1999 |
| WO | WO-00/10034 A1 | 2/2000 |
| WO | WO-03/082405 A1 | 10/2003 |

OTHER PUBLICATIONS

Ettinger et al., Mathematical Methods in Biomedical Image Analysis, Proceedings of the Workshop, Jun. 21-22, 1996, pp. 32-41.

* cited by examiner

METHOD FOR THREE-DIMENSIONAL MODELING OF THE SKULL AND INTERNAL STRUCTURES THEREOF

The invention relates to a method according to the preamble of claim 1 for three-dimensional modeling of the skull and internal structures thereof.

This patent application describes a method suited for modifying a set of magnetic resonance images taken from the head (standard head) so that the external shape of the head determined from such a set of images can be transformed to correlate with the contour of the head of another test person or patient. The present method is particularly suited to the magnetic stimulation of the brain as well as to electro-encephalography and magnetoencephalography.

In transcranial magnetic stimulation (TMS) of the brain, a coil excited with a strong current pulse of short duration is placed over the head. As a result, an electric current stimulating cerebral tissue is induced inside the skull. In order to focus the magnetic stimulation on a certain selected area of the brain, it is often necessary to resort to the magnetic resonance images taken from the test person's or patient's head. Herein, the location and orientation of the coil acting as the response-evoking means of magnetic stimulation is determined in regard to the coordinates of the patient's head with the help of a suitable localizing system. Subsequently, the location of the coil can be mapped on the magnetic resonance images (MRI) of the patient, whereupon the system operator can readily focus the stimulation on a desired area. One such method is described in FI Pat. Appl. 20021416.

Respectively, the magnetic resonance images of the patient's head are utilized when there is a need for locating a functional cerebral part in the anatomy of the brain. Brain functions can be recorded and located using conventional methods such as electro- and magnetoencephalography (EEG and MEG). Both of these methods typically use tens or even hundreds of measurement channels that sense electromagnetic fields evoked by brain activity at different points about the head or on the scalp. By knowing the exact locations of the measurement sensors relative to the head coordinates, it becomes possible to identify brain functions and to visualize the anatomical structure of each point in the magnetic resonance images.

Conventionally, the head anatomy of the patient or test person being examined is first recorded by taking anatomical magnetic resonance images or other type of images resolving anatomical structures. Next, at least three fixed marker points are selected on the head surface such that they can readily be identified on both the magnetic resonance images and the surface of the head. Advantageously, the auditory meatuses and the nasion, for instance, are chosen to serve as marker points. As a result, a coordinate transformation can be formulated suitable for identification of a point in the magnetic resonance images corresponding to a certain point on the surface of the head. Thus, e.g., the location of a TMS coil in regard to anatomical structures can be ascertained or, alternatively, a stimulus-responsive point in the brain located with the help of MEG can be located in regard to anatomical structures. Various techniques are available for making a suitable coordinate transformation. Magnetic resonance images of the test person's head are required in the implementation of this method.

Using known methods, magnetic resonance images can be deformed so as to provide correlation with the respective computer-aided tomography images. The deformation method is called image fusion. In this process, both ones of the sets of images are analyzed to find a plurality of fixed marker points that are identifiable in both image sets. Subsequently, a deforming transformation can be carried out such that the corresponding points of the images to be matched become aligned with each other.

In the art are also known methods for warping magnetic resonance images taken by MRI techniques from a test person so that the nonideal properties of magnetic resonance imaging such as the nonlinearity of gradient fields, are corrected. In these methods, correction factors are measured or computed and thereupon the images are respectively deformed. In EP patent publication 1 176 558 is further described a method for external patient contouring with the help of a suitable surface imaging system, whereupon the information thus gathered is used to deform the patient's MRI images for planning a radiotherapy treatment.

Further methods known in the art are based on deforming by dilatation and contraction warping techniques a set of MRI images taken from different persons so that first the same fixed anatomical or functional marker points are identified in the images of each one of test persons individually. Thereupon a mathematical mapping is computed individually for each test person such that the test person's MRI images are transformed in a fashion allowing the selected marker points of the deformed image sets to have the same coordinates for all the test persons. One such method is the so-called Talairach cerebral imaging system (J. Talairach and P. Tournoux, Co-planar Stereotaxic Atlas of the Human Brain, New York, Thieme Medical Publishers, Inc., 1988). The goal of this system is to deform the MRI images of different persons so that the MRI images of the different persons' brains can be compared with each other.

The above-described methods have in common that all of them need anatomical images of the test person's head.

Still further in the art are known methods in which the head contour is determined by means of an imaging system and the thus mapped surface of the head is formed into a triangulated grid that serves as a mathematical model in the computation of electro-magnetic fields associated with the use of MEG, TMS or EEG. Attempts have also been made to determine by statistical methods from the head contour such a triangulated grid that further represents the brain contour of the same test person. In this kind of method, magnetic resonance images are utilized to generate a statistical model representing correlation between the surfaces of the head contour and the brain contour. One such method is disclosed in publication D. van't Ent, J. C. de Munck, and Amanda L. Kaas, A Fast Method to Derive Realistic BEM Models for E/MEG Source Reconstruction, IEEE Trans. Biomed. Eng. (2001), BME 48(12):1434-1443. This method, however, is not used for processing MR images.

A problem hampering the use of the prior-art methods and apparatuses is that the analysis or visualization of data represented by the MRI images is possible only by taking the magnetic resonance images separately from each patient's or test person's head. Due to the high cost of magnetic resonance images of the head, also the overall cost of TMS, EEG and MEG examinations become high. Resultingly, the availability of TMS, MEG and EEG is limited.

If magnetic resonance images taken from the head of the person being examined are not available or the use thereof is not desirable, it is difficult to visualize even coarsely the area of the skull hiding a given brain region of interest. The basic reason hereto is that the head contour and size vary largely from person to person.

In a typical TMS examination, for instance, it may be desirable to focus the magnetic stimulus on the prefrontal region of the left hemisphere by placing a figure-of-eight stimulation coil at the desired area of the head. However, it is difficult to select the proper area on the head if no anatomical images of the interior structures of the head are available. Respectively in a typical MEG and EEG recording session a response is discovered relating to a certain task, which can be located inside the head in relation to marker points situated external to the head. Lacking access to anatomical images illustrating the interior structures of the head, however, it is difficult to tell the anatomical part of the brain that coincides with the identified point of response.

In another typical MEG or EEG examination, the task may be to identify brain activity at two different regions of the brain as a response to, e.g., a task involving motor skills. In this exemplary case, the first region can be positively identified based on such variables, among others, as the characteristic waveform of the response to represent the function of the motor cortex, while the anatomical locus of the other component of the response cannot be located without resorting to magnetic resonance imaging or other techniques such as computer-aided tomography suited for resolving anatomical structures.

It is an object of the present invention to provide an entirely novel kind of method capable of overcoming the problems of the above-described prior art.

Accordingly, the invention strives to achieve a fully new approach to the approximate localization of the major brain regions in a test person's head without the need for magnetic resonance imaging. The method is particularly useful in the focusing of magnetic stimulation and in the interpretation and visualization of results obtained by means of magnetic stimulation, EEG and MEG. This facility can be employed, e.g., for making screening measurements for large groups of patients without the need for taking costly MRI images from each patient individually.

The goal of the invention is attained by virtue of modeling the coordinates of the test person's head as to its different internal anatomical regions and particularly its different brain regions on the basis of the test person's head contour and, additionally, on the basis of the different internal anatomical regions, particularly its different brain regions, actually recorded from the head of another test person.

More specifically, the method according to the invention is characterized by what is stated in the characterizing part of claim 1.

The invention offers significant benefits.

One major advantage is that the patient need not be subjected to magnetic resonance imaging to identify the internal anatomy of the patient's head for proper focusing of magnetic stimulation or analysis of MEG and EEG recordings.

Another advantage is that the method allows the stimulation responses of different patients to be compared with each other in the coordinate system of a "standard head".

A third advantage is that a deforming image transform can be carried out or refined using functional marker points identified in the interior volume of the brain.

A still further advantage is that the method makes it possible to readily indicate without anatomical imaging the coarse coordinates of a point on the head surface under which a given anatomical brain region is located. Furthermore a coarse location of a given brain anatomical region under a selected point on the head surface is possible without the need for magnetic resonance imaging.

In the following the invention will be examined with the help of exemplary embodiments and by making reference to the appended drawing in which FIG. 1 is a schematic illustration showing the use of a method according to the invention in a single plane.

Referring to FIG. 1, the upper diagram shows a single plane of accurate magnetic resonance images taken from the head of a test person B. Test person A is measured only for the external dimensions of the head in order to draw the sectional plane A shown in the middle diagram. According to the invention, the coordinate data of diagram B are dilated and/or contracted (that is, scaled) so as to fit the data within the confines of sectional plane A, whereby the diagram of sectional plane A is transformed into a modeled sectional diagram A'. In the exemplary case, it has been necessary to dilate the diagram shape of sectional plane B in the vertical direction and to contract in the horizontal direction.

The above-described procedure is applied entirely identically also in the height direction, whereby three-dimensional modeling is attained.

Accordingly, the invention is based on using a method wherein the head contour of the person (first person A) being examined is determined by measuring the coordinates of selected marker points on the scalp with the help of a localization system. Advantageously, the number of measured marker points is some tens and they are located at different sides of the head. The greater the number of measured marker points the better is the result of the deformation process. Already five marker points on the head (forehead, left side, right side occipital protuberance and parietal top) give relatively accurate results. Next, the head contour of some other person (person B) is determined from magnetic resonance images taken earlier from this person's head. The images of person B are deformed (scaled) computationally using translation, rotation and linear and/or nonlinear deformation so as to make the shape of the head images correlate with the contour of the person's scalp, whereby a deforming linear or nonlinear transformation between both shapes takes place. The head images taken from person B may also be called a standard head. In the method the transformation is applied volumetrically to the entire sets of magnetic resonance images, that is, also to coordinates located in the interior volume of the head. Herein the location and shape of the anatomical structures may become distorted. It is also possible to use a plurality of standard heads (e.g., separately for adults and children), whereby a standard head of closest fit can be individually selected for each patient. Also the racial differences between head contours can be taken into account by maintaining a selection of different standard heads. Advantageously, the standard head is computed using a set of MRI images having a good resolution, e.g., 256×256 pixels in each sectional plane.

Image deformation (scaling) can be carried out, for instance, in the following manner. First, the magnetic resonance images of the standard head, that is, those taken from the head of person B, covering an entire sectional plane of the head are segmented by determining the coordinates of selected marker points on the skull surface. Next, selected points of the scalp of person A being examined are determined in the earlier described fashion using a localizing system. Thereupon a suitable linear or nonlinear deformation algorithm is carried out such that the magnetic resonance images of person B are deformed maximally well to correlate with the head shape of person A. The deformation transform may also be incomplete, whereby the shapes of the two heads are not aggressively deformed to full correlation. Suitable deformation algorithms are extensively described in the literature of the art. The magnetic resonance images can be represented digitally in any known graphic format such as pixel or vector graphics.

One exemplary deformation technique comprises determining from the magnetic resonance images of person B the location of, e.g., five marker points (the left and right auditory meatuses, the nasal bend also called the nasion, the occipital protuberance also called the inion and the parietal top). The respective marker points are determined with the help of localizing system from the head surface of the person being examined. First, the marker points are registered with each other by way of carrying out a transformation that by translation and rotation makes the respective marker points of the heads of persons A and B to converge with each other. Subsequently, a linear scaling algorithm can be applied to the magnetic resonance images of test person B can be subjected to linear scaling such that the respective marker points unite with each other. As a result, a deforming transform takes place capable of making the head shape identified from the magnetic resonance images of person B to correlate coarsely with the head shape of person A. When necessary, the procedure may be similarly extended to correlation of a larger number of marker points.

One possible deformation procedure comprises the use of an algorithm described in publication J. Lötjönen, et al.: Model Extraction from Magnetic Resonance Volume Data Using the Deformable Pyramid, Medical Image Analysis, Vol. 3, No. 4, pp. 387406, 1999). First, the magnetic resonance images of person B are processed to determine marker points on the head surface, e.g., by image thresholding. The head contour of person A is determined at N points using a localizing system. Both sets of points are registered with each other by way of performing translation and rotation operations such that make the sets of points to converge with each other maximally well. When using optimally selected translation and rotation operators, one possible strategy is, for instance, to aim at a minimum sum of squares of differences between local radii of curvature on the correlating surfaces. Next, the magnetic resonance images are divided into a cubic grid of 3×3×3 voxels. An energy function E is defined that may be, e.g., the sum of distances from the points of image set A to the respective next closest point of image set B. Also for each elementary cube of the grid is written a deformation function f(x,y,z) that typically is a spline or polynomial function (such as Bernstein polynomials) and thus defines the amount of translation at other points of the cubic grid caused by a shift of one corner point of the grid. Generally, the amount of grid deformation becomes the smaller the larger the distance of the grid point from the corner point. The deformation function may be linear or nonlinear. Next, the locations of the grid points are translated so as to minimize energy function E. As a result, the elementary cubes of the initially perfect cubic grid are dilated or contracted and thus deformed. The deformation function f is applied to each elementary cube. After the minimization of energy function E, the surfaces of the heads correlate with each other. In practice, also certain boundary conditions must be defined for the cubic grid. For instance, it may be advantageous to confine the dilation of the individual elementary cubes so that the dilation of all elementary cubes is uniform. Such a suitable boundary condition may be implemented in energy function E.

In another embodiment of the invention, also functional marker points of the brain may be utilized. Herein, the localization of the motor cortex area of a person being examined but not having MR images of the head available can be carried out by magnetic stimulation or, alternatively, using electroencephalography or magnetoencephalography or infrared tomography. Localization is performed relative to external marker points of the head (e.g., ears and nose). Similar localization is performed in beforehand for another person (person B serving as a standard head) for whom the magnetic resonance images of the head are available. The localization of the motor cortex of person B is performed from the MR images. The set of magnetic resonance images is warped so as to make the locations of the motor cortex of the patient and the second person to correlate. Additionally, the MR images of person B are deformed so as to bring them into at least partial correlation with the head shape of the person being examined. A similar procedure is also applicable to the utilization of multiple different functional marker points such as the motor or visual cortical areas of both hemispheres. When so desired, it is also possible to utilize herein the location of such a functional marker point that has been determined by statistical methods for a plurality of persons.

An example of the use of functional marker points in image deformation is represented by TMS. With the help of this method, the location of the motor cortex can be readily determined by moving the stimulation coil over the head until the strongest muscle response (recorded by EMG) is detected in the hand muscles of the opposite side of the body. The same localization may be carried out for both hemispheres. Using suitable weights in the deformation procedure, the motor cortex locations of the person being examined and person B are made to coincide with each other.

An essential feature of the present method is that the locations of the magnetic stimulation coil, the EEG electrodes or the MEG sensors are measured relative to the test person's head coordinates using a localization system. Herein, on the person's head is mounted a position sensor whose location can be determined with the help of a localization system. The localization system is used for determining at least three marker points of the head (such that may also be identified in the MRI images), whereupon the deformation of the image coordinates can be performed. The localization system used in the invention can be based, e.g., on infrared radiation or electromagnetic fields. This kind of equipment is commercially marketed, e.g., by a Canadian company Northern Digital Inc., for instance.

In the context of the present application, scaling refers to a data processing method in which data generally representing an image is transformed into another form by linear or nonlinear procedures of dilatation/contraction warping of the image. An alternative term for this operation is deformation.

What is claimed is:

1. A method for modeling, with a processor, different functional areas of a brain within a second head to focus magnetic stimulation and/or visualize the results of magnetic stimulation techniques, magnetoenecephalography (MEG) or electroencephalography (EEG), the method comprising:
   a) determining the location of at least one functional area of a brain within a first head in three-dimensional space,
   b) determining the external dimensions of the second head, and
   c) scaling, with a processor, location data of said at least one functional area of said first head in three-dimensional space to correlate with said external dimensions of said second head, thereby defining the locations of the at least one functional area in said second head such that the location data of the functional areas of the brain of said second head are modeled without anatomical images of the internal structures of said second head.

2. The method of claim 1, further comprising focusing magnetic stimulation and/or visualization of results obtained by magnetic stimulation, MEG or EEG based on results of said scaling location data.

3. The method of claim 1, wherein said location data is displayed in an image format and the scaling thereof in step c) is implemented by mutual moving of individual pixels.

4. The method of claim 1, wherein a response recorded by MEG or EEG or, alternatively, an effective stimulating field of trans-cranial magnetic stimulation (TMS) is localized in relation to anatomical marker points determined on the second head surface.

5. The method of claim 1, wherein said step b) of determining the external head dimensions is performed by using infrared light, electromagnetic fields, laser light or a pointer equipped with electrical position sensor means.

6. The method of claim 1, wherein said step a) of determining uses internal structures of a plurality of heads of persons of substantially the same age;
   said step c) of scaling uses an image scaling algorithm and includes adjusting the distance from the cortex to the scalp to a value typical for the persons of substantially the same age.

7. The method of claim 1, wherein the step c) of scaling performs a deformation operation utilizing location data of such functional points of the brain that are localized solely with the help of magnetic stimulation, MEG or EEG as functional points of the brain.

8. The method of claim 1, wherein said step of scaling performs image deformation using a minimizing algorithm that minimizes the mutual distances between the respective points of the deformed image of the second head and the points measured on the surface of a first head.

9. The method of claim 8, wherein the computation results of the minimization algorithm are accepted even when the mutual distances between respective image points are not reduced to zero.

10. The method of claim 1, further comprising generating visual results of TMS, BEG or MEG examinations performed on a patient having no magnetic resonance images of his/her head available.

11. The method of claim 1, further comprising displaying results in a single set of MR images obtained from measurements performed on a plurality of test persons.

12. The method of claim 1, further comprising selecting, as a first head, a head from a library of plural magnetic resonance images taken from a plurality of persons representing heads of different types and shapes.

13. The method of claim 1, wherein scaling comprises linear scaling.

14. The method of claim 1, wherein scaling comprises nonlinear scaling.

15. The method of claim 1, wherein the method further comprises d) obtaining a three-dimensional image from magnetic resonance imaging or computer-aided tomography of the first head.

16. The method of claim 1 wherein the step b) only determines the external dimensions of the second head without directly determining the location of internal structures of the second head in three dimensional space.

17. The method of claim 16 wherein the step b) is performed without acquiring or generating any information regarding the location of internal structures of the second head.

\* \* \* \* \*